(12) United States Patent
Xu

(10) Patent No.: US 9,598,425 B2
(45) Date of Patent: Mar. 21, 2017

(54) METHOD FOR PREPARING IBRUTINIB

(71) Applicant: SUZHOU MIRACPHARMA TECHNOLOGY CO., LTD., Suzhou (CN)

(72) Inventor: Xuenong Xu, Suzhou (CN)

(73) Assignee: SUZHOU MIRACPHARMA TECHNOLOGY CO., LTD., Suzhou (CN)

( * ) Notice: Subject to any disclaimer, the term of this patent is extended or adjusted under 35 U.S.C. 154(b) by 0 days.

(21) Appl. No.: 15/159,600

(22) Filed: May 19, 2016

(65) Prior Publication Data

US 2016/0264584 A1    Sep. 15, 2016

Related U.S. Application Data

(63) Continuation of application No. PCT/CN2014/088178, filed on Oct. 9, 2014.

(30) Foreign Application Priority Data

Nov. 20, 2013 (CN) .......................... 2013 1 0589969

(51) Int. Cl.
  *C07D 487/00* (2006.01)
  *C07D 487/04* (2006.01)
(52) U.S. Cl.
  CPC .................................. *C07D 487/04* (2013.01)
(58) Field of Classification Search
  None
  See application file for complete search history.

(56) References Cited

U.S. PATENT DOCUMENTS

| | | |
|---|---|---|
| 2008/0058528 A1 | 3/2008 | McDermott et al. |
| 2008/0108636 A1 | 5/2008 | Honigberg et al. |
| 2009/0050897 A1 | 2/2009 | Watanabe |
| 2010/0254905 A1 | 10/2010 | Honigberg et al. |
| 2011/0039190 A1 | 2/2011 | Owejan et al. |

FOREIGN PATENT DOCUMENTS

| | | |
|---|---|---|
| CN | 102746305 A | 10/2012 |
| CN | 103121999 A | 5/2013 |
| CN | 103626774 A | 3/2014 |
| WO | 2013003629 A2 | 1/2013 |

OTHER PUBLICATIONS

Pan Zhengying et al. Discovery of selective irreversible inhibitors for bruton's tyrosine kinase. ChemMedChem, No. 1, vol. 2, Dec. 12, 2006 (Dec. 12, 2006) p. 59, Scheme 1.

*Primary Examiner* — Jeffrey H Murray
(74) *Attorney, Agent, or Firm* — Perkins Coie LLP

(57) ABSTRACT

Provided is a method for preparing Ibrutibin (I), and steps of preparing same comprise: 4-benzyloxybenzoyl chloride (II) is used as a raw material, condensation and methoxidation reactions occur among 4-benzyloxybenzoyl chloride (II), malononitrile, and dimethyl sulfate to generate 4-benzyloxy-phenyl(methoxy)vinylidenedicyanomethane (III), pyrazole cyclization occurs between the intermediate (III) and 1-(3R-hydrazino-1-piperidino)-2-propylene-1-ketone (IV) to acquire 1-[(3R)-[3-(4-benzyloxyphenyl)-4-nitrile-5-amino-1H-pyrazole]-1-piperidino]-2 propylene-1-ketone (V), and pyrimidine cyclization occurs between an intermediate (V) and a cyclizing agent to prepare Ibrutinib (I). In the preparation method, the raw material is readily available, and the process is simple, economical, environmentally friendly, and is suitable for industrial production.

8 Claims, No Drawings

METHOD FOR PREPARING IBRUTINIB

CROSS REFERENCE TO RELATED APPLICATIONS

This application is a continuation of PCT NO. PCT/CN2014/088178 filed Oct. 9, 2014, which claims priority to CN 201310589969.2 filed Nov. 20, 2013, both of which are incorporated herein by reference.

TECHNICAL FIELD

This invention relates to the technical field of organic synthesis route design and preparation of API and intermediates, in particular, to a method for preparing Ibrutinib.

BACKGROUND ART

Ibrutinib is A Bruton tyrosine kinase (BTK) inhibitor jointly developed by U.S. Johnson & Johnson and Pharmacyclics Inc. Since the compound has no standard Chinese translation, the applicant translated it as "Yilutini". In February 2013, this drug received the qualification of "Breakthrough Therapy" by US Food and Drug Administration (FDA), and on Nov. 13, 2013, it was approved to appear on the markets. As a single treatment drug of mantle cell lymphoma, it is applicable to patients of mantle cell lymphoma previously treated by other means. Its trade name is Imbruvca. Ibrutinib is the first drug targeting BTK inhibitors appearing on the markets.

The chemical name of Ibrutinib is 1-[(3R)-3-[4-amino-3-(4-phenoxyphenyl) 1H-pyrazolo[3,4-D]pyrimidine-1-yl]-1-piperidinyl]-2-propen-1-one, having the structural formula as below:

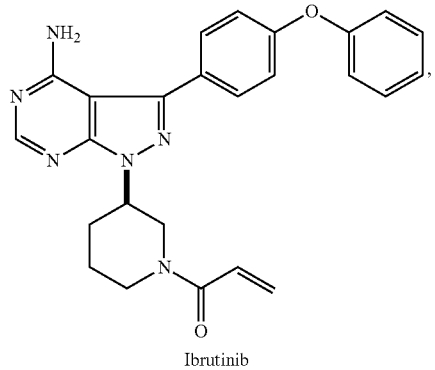

Ibrutinib

The methods for preparing Ibrutinib were reported. US Patent No. US20080108636, No. US2008058528, No. US2009050897, No. US2010254905 and No. US2011039190 reported the synthesis of Ibrutinib and its analogs. In this method, 4-phenoxy-benzoic acid is used as starting material, after acylation, condensation, methoxylation, pyrazole cyclization, pyrimidine cyclization, N-alkylation, deprotection and acryloyl reaction, etc., functional groups are added, to finally prepare the target product. However, this routine needs a number of steps and a variety of unconventional materials and reagents, especially the trimethylsilyl diazomethane and polymer-supported triphenylphosphine have potential hazards and environmental pollution, thus, it is not suitable for industrial production.

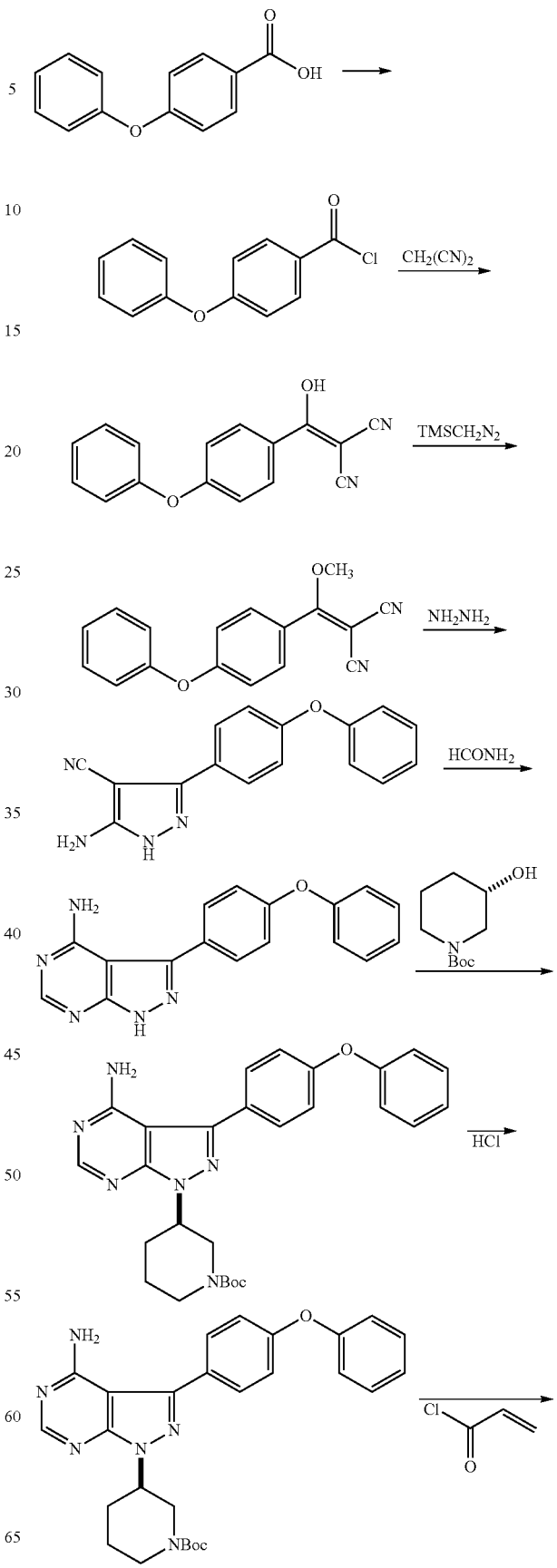

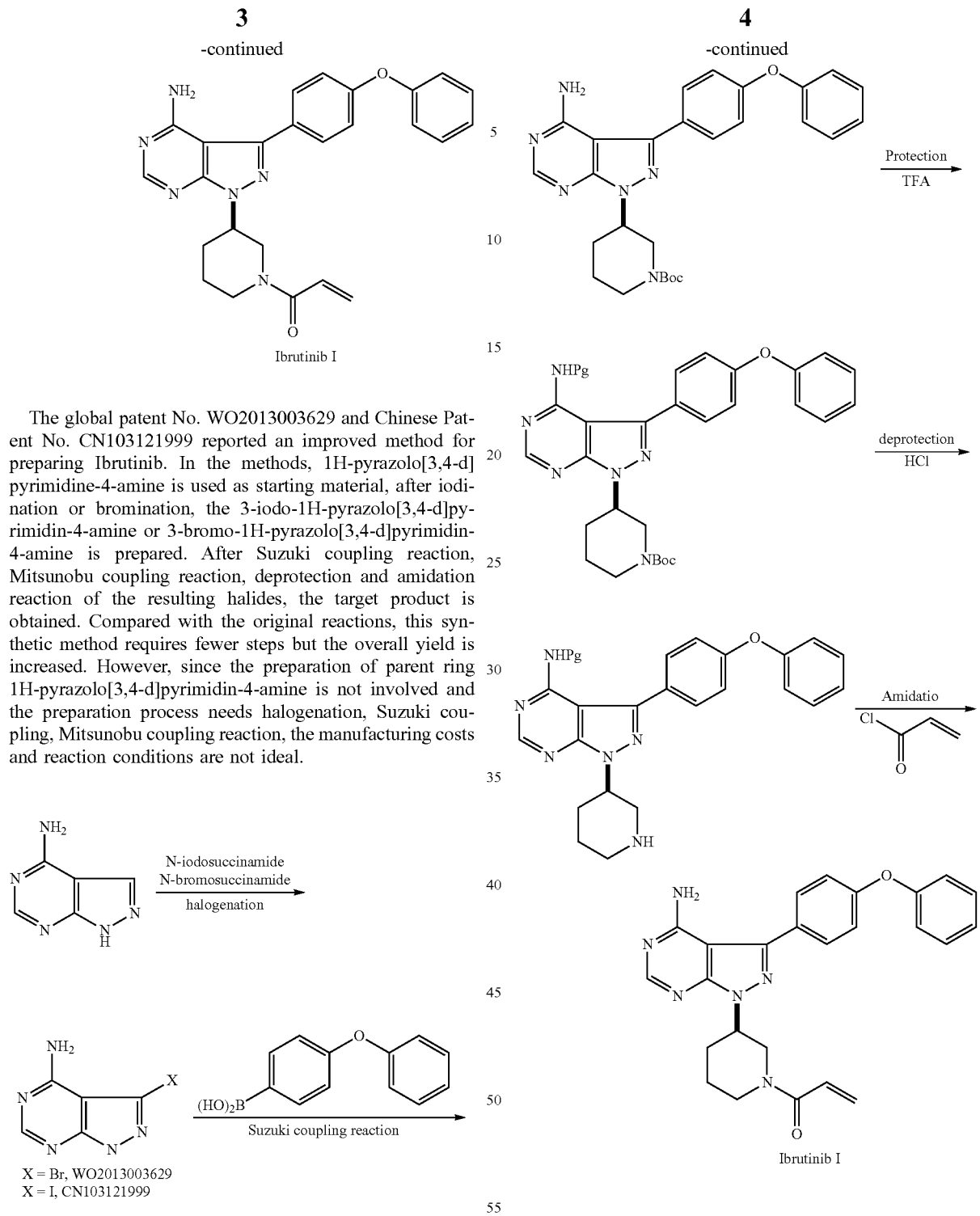

The global patent No. WO2013003629 and Chinese Patent No. CN103121999 reported an improved method for preparing Ibrutinib. In the methods, 1H-pyrazolo[3,4-d]pyrimidine-4-amine is used as starting material, after iodination or bromination, the 3-iodo-1H-pyrazolo[3,4-d]pyrimidin-4-amine or 3-bromo-1H-pyrazolo[3,4-d]pyrimidin-4-amine is prepared. After Suzuki coupling reaction, Mitsunobu coupling reaction, deprotection and amidation reaction of the resulting halides, the target product is obtained. Compared with the original reactions, this synthetic method requires fewer steps but the overall yield is increased. However, since the preparation of parent ring 1H-pyrazolo[3,4-d]pyrimidin-4-amine is not involved and the preparation process needs halogenation, Suzuki coupling, Mitsunobu coupling reaction, the manufacturing costs and reaction conditions are not ideal.

SUMMARY OF THE INVENTION

The object of the invention is to overcome the drawbacks of the prior art and provide a method for preparing Ibrutinib. The method has readily available raw materials, simple process, and it is economical and environmentally friendly, and suitable for industrial production.

To achieve the above object, the present invention adopts the following main technical solutions: a method for preparing Ibrutinib (I),

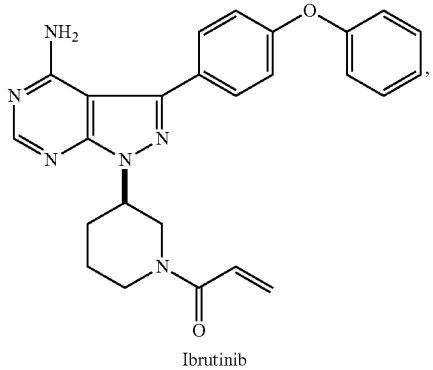

Ibrutinib

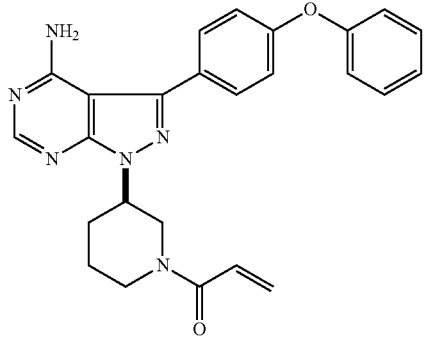

Ibrutinib I wherein the preparation steps comprise: 4-benzyloxybenzoyl chloride (II) is used as a raw material, condensation and methoxidation reactions occur among 4-benzyloxybenzoyl chloride (II), malononitrile, and dimethyl sulfate to generate 4-benzyloxyphenyl(methoxy)vinylidenedicyanomethane (III), pyrazole cyclization occurs between the intermediate (III) and 1-(3R-hydrazino-1-piperidino)-2-propylene-1-ketone (IV) to acquire 1-[(3R)-[3-(4-benzyloxyphenyl)-4-nitrile-5-amino-1H-pyrazole]-1-piperidino]-2 propylene-1-ketone (V), and pyrimidine cyclization occurs between the intermediate (V) and a cyclizing agent to prepare Ibrutinib (I).

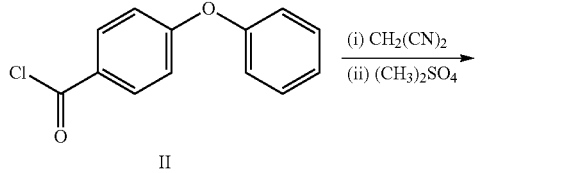

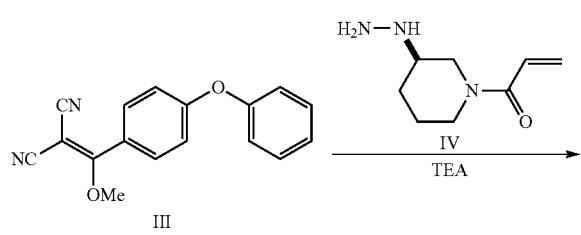

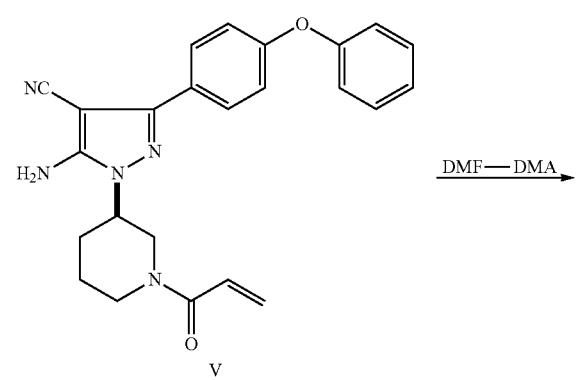

In addition, the invention further provides the following additional technical solutions:

In the condensation and methoxidation reactions, the feeding molar ratio of 4-benzyloxybenzoyl chloride(II), malononitrile and dimethyl sulfate is 1:1-2:2-4, preferably 1:1-1.2:3-4.

In the pyrazole cyclization, the feeding molar ratio of 4-benzyloxyphenyl(methoxy)vinylidenedicyanomethane (III) to 1-(3R-hydrazino-1-piperidino)-2-propylene-1-ketone(IV) is 1:0.5-1.5, preferably 1:1.

The temperature of pyrazole cyclization is 50-120° C., preferably 80-90° C.

The solvents used in pyrazole cyclization are xylene, toluene, tetrahydrofuran, methanol, ethanol, isopropanol, n-butanol, dioxane, N,N-dimethylformamide or dimethyl sulfoxide, preferably ethanol or toluene.

In the pyrimidine cyclization, the feeding molar ratio of 1-(3R-hydrazino-1-piperidino)-2-propylene-1-ketone(IV) to cyclizing agent is 1:1-2, preferably 1:1.5.

The cyclizing agents used in pyrimidine cyclization are trimethyl orthoformate, triethyl orthoformate, formic acid, formamide, triazine, N,N-dimethylformamide, N,N-diethylformamide or N,N-dimethylformamide dimethyl acetal, preferably formamide or N,N-dimethylformamide dimethyl acetal.

The temperature of pyrimidine cyclization is 50-150° C., preferably 100-110° C.

Compared to prior art, the method for preparing Ibrutinib (I) in the invention has the features: easily available raw materials, simple process, economical and environmentally-friendly, etc., therefore, it is suitable for industrial production, to facilitate the economical and technological development of the API.

DETAILED DESCRIPTION OF THE PREFERRED EMBODIMENTS

The invention is further described in details in combination with several preferred embodiments.

Embodiment I 6.6 g of malononitrile (6.6 g, 0.1 mol), 4.8 g of sodium hydride (4.8 g, 0.2 mol, 80% dispersed in paraffin) and 100 mL of freshly-treated anhydrous tetrahydrofuran were added to a three-neck reaction flask, added dropwise with 50 mL of 4-benzyloxybenzoyl chloride (II) (23.2 g, 0.1 mol) in tetrahydrofuran solution while stirring; after reaction 2 hours under room temperature, 250 mL of 1M dilute hydrochloric acid was added to react 30 min while stirring, then extracted three times with ethyl acetate. The organic phases were combined and dried over anhydrous magnesium sulfate, concentrated to get the solid, dissolved in 150 mL of dioxane and 50 mL of saturated sodium bicarbonate solution, then dimethyl sulfate (37.8 g, 0.3 mol) was added to heat to 80-90° C. and react 3 hours while stirring, to complete the reaction detected by TLC. 400 mL of deionized water was added, and extracted with methyl tert-butyl ether three times; then the organic phases were combined and dried over anhydrous sodium sulfate. The solvent was recovered under a reduced pressure and the resulting crude product was recrystallized by methanol to get 17.6 g of white solid 4-benzyloxyphenyl (methoxy)vinylidenedicyanomethane (III), with a yield of 63.8%.

Embodiment II 13.8 g of 4-benzyloxyphenyl (methoxy)vinylidenedicyanomethane (III) (13.8 g, 50 mmol), 8.5 g of 1-(3R-hydrazino-1-piperidino)-2-propylene-1-ketone (IV) (8.5 g, 50 mmol) and 200 mL of ethanol were added to a three-neck reaction flask, added dropwise with triethylamine (5 g, 50 mmol) while stirring; heated to reflux and react 5 hours while stirring, to complete the reaction detected by TLC. The solution was concentrated under reduced pressure, and deionized water was added to the residue, stirred at room temperature for crystallization, filtered, and the resulting solid was recrystallized by ethanol and water (1:1) to get 16.6 g of off-white solid 1-[(3R)-[3-(4-benzyloxyphenyl)-4-nitrile-5-amino-1H-pyrazole]-1-piperidino]-2 propylene-1-ketone (V), with a yield of 80.4%.

Embodiment III 4.13 g of 1-[(3R)-[3-(4-benzyloxyphenyl)-4-nitrile-5-amino-1H-pyrazole]-1-piperidino]-2 propylene-1-ketone (V) (4.13 g, 10 mmol), 1.19 g of N,N-dimethylformamide dimethyl acetal (1.19 g, 15 mmol), and 50 mL of toluene were added to a three-neck reaction flask, added with 3 mL of acetic acid while stirring, heated to 105-110° C., and then the resulting methanol was separated by an oil-water separator, reacting 3 hours at constant temperature, and the reaction was detected by TLC. Toluene was removed by concentration under reduced pressure, then 30% concentrated aqueous ammonia was added to the residue to separate solids. Under the stirring condition, the solution was heated to reflux, and 3 hours later, the reaction was detected by TLC; cooled down to room temperature to separate out solids, crystallized with slow stirring for 12 hours, filtered and the crude product was recrystallized by ethanol to get 3.2 of Ibrutinib (I) 3.2 g, with a yield of 72.7%.

The foregoing invention has been described in detail by way of illustration and example for purposes of clarity and understanding. As is readily apparent to one skilled in the art, the foregoing are only some of the methods and compositions that illustrate the embodiments of the foregoing invention. It will be apparent to those of ordinary skill in the art that variations, changes, modifications and alterations may be applied to the compositions and/or methods described herein without departing from the true spirit, concept and scope of the invention.

What is claimed is:
1. A method for preparing Ibrutinib(I),

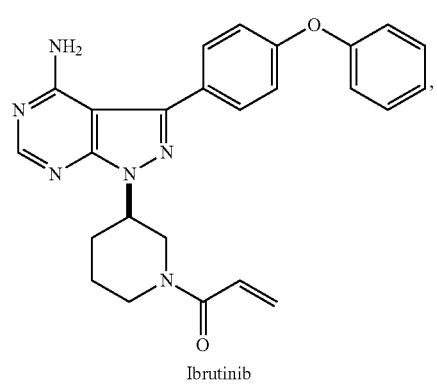

Ibrutinib wherein the preparation steps comprise: 4-benzyloxybenzoyl chloride (II) is used as a raw material, condensation and methoxidation reactions occur among 4-benzyloxybenzoyl chloride (II), malononitrile, and dimethyl sulfate to generate 4-benzyloxyphenyl (methoxy)vinylidenedicyanomethane (III), pyrazole cyclization occurs between the intermediate (III) and 1-(3R-hydrazino-1-piperidino)-2-propylene-1-ketone (IV) to acquire 1-[(3R)-[3-(4-benzyloxyphenyl)-4-nitrile-5-amino-1H-pyrazole]-1-piperidino]-2 propylene-1-ketone (V), and pyrimidine cyclization occurs between the intermediate (V) and a cyclizing agent to prepare Ibrutinib (I).

2. The method for preparing Ibrutinib(I) according to claim 1, wherein the feeding molar ratio of 4-benzyloxybenzoyl chloride(II), malononitrile and dimethyl sulfate is 1:1-2:2-4.

3. The method for preparing Ibrutinib(I) according to claim 1, wherein the feeding molar ratio of 4-benzyloxyphenyl(methoxy)vinylidenedicyanomethane 1-(3R-hydrazino-1-piperidino)-2-propylene-1-ketone(IV) is 1:0.5-1.5.

4. The method for preparing Ibrutinib(I) according to claim 3, wherein the temperature of pyrazole cyclization is 50-120° C.

5. The method for preparing Ibrutinib(I) according to claim 3, wherein the solvents used in pyrazole cyclization are xylene, toluene, tetrahydrofuran, methanol, ethanol, isopropanol, n-butanol, dioxane, N,N-dimethylformamide or dimethyl sulfoxide.

6. The method for preparing Ibrutinib(I) according to claim 1, wherein the feeding molar ratio of 1-(3R-hydrazino-1-piperidino)-2-propylene-1-ketone(IV) to cyclizing agent is 1:2 in the pyrimidine cyclization.

7. The method for preparing Ibrutinib(I) according to claim 6, wherein the cyclizing agents used in pyrimidine cyclization are trimethyl orthoformate, triethyl orthoformate, formic acid, formamide, triazine, N,N-dimethylformamide, N,N-diethylformamide or N,N-dimethylformamide dimethyl acetal.

8. The method for preparing Ibrutinib(I) according to claim 6, wherein the temperature of pyrimidine cyclization is 50-150° C.

* * * * *